United States Patent [19]

Rosenberg

[11] 4,342,316
[45] Aug. 3, 1982

[54] ZERO STASIS CATHETER

[75] Inventor: Philip Rosenberg, Gurnee, Ill.

[73] Assignee: The Kendall Company, Boston, Mass.

[21] Appl. No.: 280,741

[22] Filed: Jul. 6, 1981

[51] Int. Cl.$^3$ .............................................. A61M 25/00
[52] U.S. Cl. ................................................... 128/349 B
[58] Field of Search ............ 128/349, 349 B, 349 BV, 128/325, 344

[56] References Cited

U.S. PATENT DOCUMENTS

| | | | |
|---|---|---|---|
| 2,473,742 | 6/1949 | Auzin | 128/349 |
| 2,849,001 | 8/1958 | Oddo | 128/349 B |
| 3,045,677 | 7/1962 | Wallace | 128/349 B |
| 3,394,705 | 7/1968 | Abramson | 128/349 B |
| 3,438,375 | 4/1969 | Ericson et al. | 128/349 |
| 3,811,448 | 5/1974 | Morton | 128/349 B |
| 3,889,686 | 6/1975 | Duturbure | 128/349 B |
| 3,954,110 | 5/1976 | Hutchinson | 128/349 B |
| 4,040,413 | 8/1977 | Ohshiro | 128/6 |
| 4,117,815 | 12/1979 | Patel | 128/349 B |
| 4,198,981 | 4/1980 | Sinnreich | 128/344 |
| 4,219,026 | 8/1980 | Layton | 128/349 B X |
| 4,233,983 | 11/1980 | Rocco | 128/349 B |

FOREIGN PATENT DOCUMENTS 2823192 10/1977 Fed. Rep. of Germany .

Primary Examiner—Stephen C. Pellegrino
Attorney, Agent, or Firm—Powell L. Sprunger

[57] ABSTRACT

A catheter comprising, an elongated shaft having an inflation lumen extending along the shaft, and a drainage lumen extending through the shaft. The catheter has a proximal end, a distal end, and a distal end portion. The catheter also has an elastic sleeve on the distal end portion of the catheter and having opposed ends. The sleeve is bonded to the distal end portion in spaced circumferential zones adjacent the opposed ends of the sleeve and along longitudinal lines at least a substantial distance between the zones on opposed sides of the distal end portion. The catheter has an inflation opening beneath the sleeve communicating with the inflation lumen, and at least one drainage eye proximal the sleeve and communicating with the drainage lumen.

14 Claims, 21 Drawing Figures

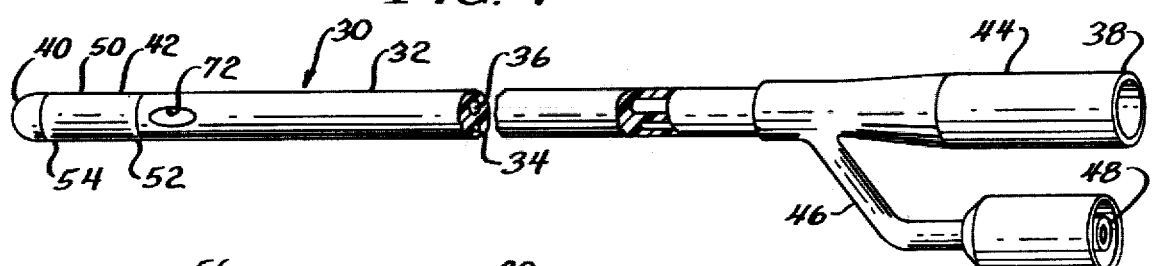
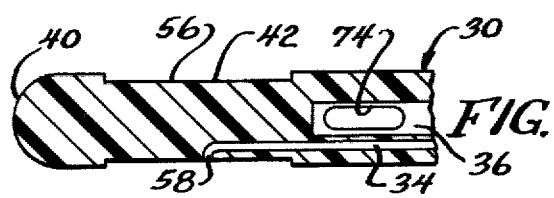
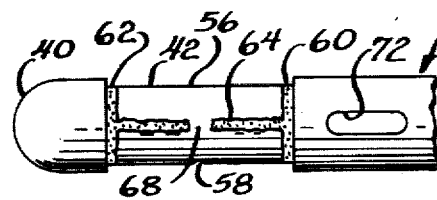
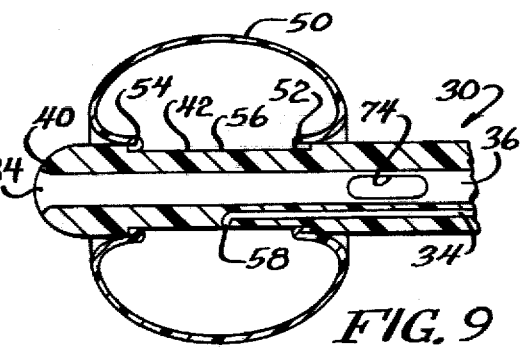
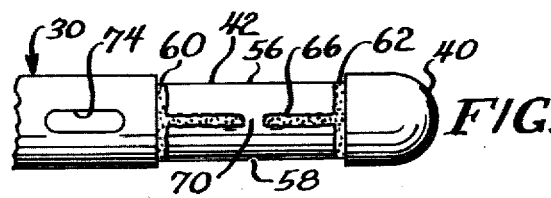
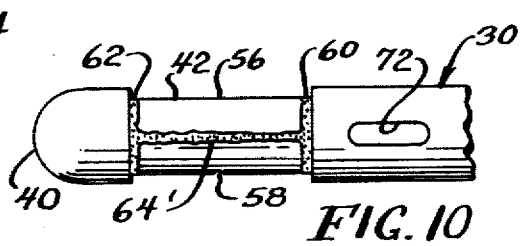
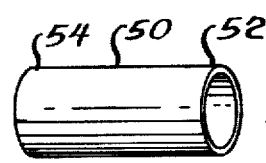
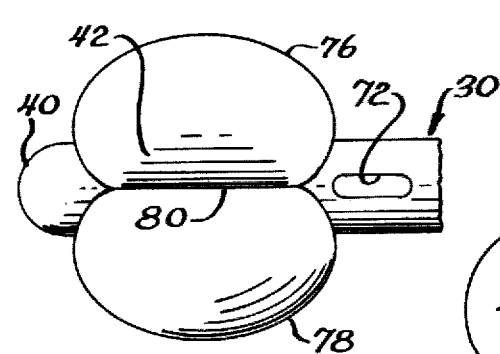
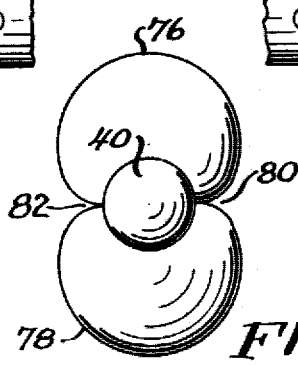
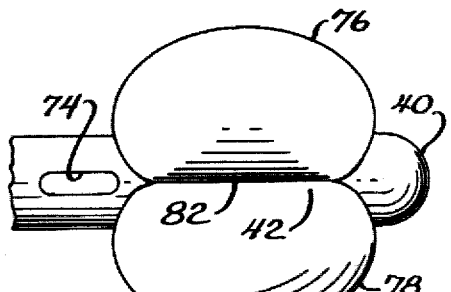

ZERO STASIS CATHETER

BACKGROUND OF THE INVENTION

The present invention relates to liquid drainage systems, and more particularly to catheters.

In the past, urinary or Foley catheters have been proposed for draining urine from a patient's bladder. Such catheters generally comprise an elongated shaft having an inflation lumen and drainage lumen extending through the shaft. The catheters have an inflatable balloon on a distal end portion of the catheter, with the inflation lumen communicating with the balloon. The catheters also have one or more drainage eyes distal the balloon communicating with the drainage lumen. In use, the catheter is passed through the patient's urethra until the balloon is located in the bladder. The balloon is then inflated to retain the catheter in place. During catheterization, urine drains through the drainage eyes and drainage lumen to a drainage tube connected to the catheter and to a drainage bag for collection therein.

Although in widespread use, such catheters are deficient in a number of respects. First, the drainage eyes in the placed catheter are spaced a considerable distance from the bladder neck, and the catheters do not accomplish complete drainage from the bladder. Also, the catheters protrude a considerable distance into the bladder, and cause irritation against the opposite blader wall in the patient's body.

SUMMARY OF THE INVENTION

A principal feature of the present invention is the provision of an improved catheter for draining liquid from the body of a patient.

The catheter of the present invention comprises, an elongated shaft having an inflation lumen extending along the shaft, and a drainage lumen extending through the shaft. The catheter has a proximal end, a distal end, and a distal end portion. The catheter also has an elastic sleeve on the distal end portion of the catheter and having opposed ends. The catheter has means bonding the sleeve to the distal end portion in spaced circumferential zones adjacent the opposed ends of the sleeve and along longitudinal lines at least a substantial distance between the zones on opposed sides of the distal end portion. The catheter has an inflation opening beneath the sleeve communicating with the inflation lumen, and at least one drainage eye proximal the sleeve and communicating with the drainage lumen.

A feature of the present invention is that the inflated balloon defines opposed channels to permit drainage of liquid to the proximal drainage eyes.

Another feature of the invention is that the catheter accomplishes improved drainage from the patient's bladder, since the drainage eyes of the placed catheter are located adjacent the bladder neck.

Yet another feature of the invention is that the catheter has a shorter length of protrusion into the bladder, and the catheter provides less chance of irritation from the distal end of the catheter against the opposite bladder wall.

Still another feature of the invention is that the distal end portion of the catheter may be tapered to permit easier insertion of the catheter through the patient's urethra.

Further features will become more fully apparent in the following description of the embodiments of this invention and from the appended claims.

DESCRIPTION OF THE DRAWINGS

In the drawings:

FIG. 1 is a fragmentary elevational view taken partly in section of a catheter of the present invention;

FIG. 2 is a sectional view of a distal end portion of the catheter of FIG. 1;

FIGS. 3 and 4 are fragmentary elevational views of the catheter taken from opposed sides of the catheter;

FIG. 5 is a perspective view of a sleeve for the catheter of FIG. 1;

FIGS. 6 and 7 are fragmentary elevational views taken from opposed sides of the catheter of the inflated sleeve for the catheter of FIG. 1;

FIG. 8 is an end view of the inflated sleeve for the catheter of FIG. 1;

FIG. 9 is a fragmentary sectional view of another embodiment of the catheter of the present invention;

FIG. 10 is a fragmentary elevational view of another embodiment of the catheter of the present invention;

DESCRIPTION OF THE PREFERRED EMBODIMENTS

Figure 11:
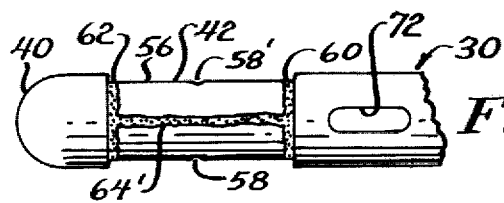
FIGS. 11 and 12 are fragmentary elevational views taken from opposed sides of the catheter of another embodiment of the catheter of the present invention.

Referring now to FIGS. 1-5, there is shown a catheter generally designated 30 having an elongated shaft 32 with an inflation lumen 34 extending through the shaft, and with a drainage lumen 36 extending through the shaft 32. The catheter 30 has a proximal end 38, a distal end 40, and a distal end portion 42. The catheter 30 has a connector 44 adjacent the proximal end 38 of the catheter 30, with the connector 44 defining a continuation of the drainage lumen 36. The catheter 30 has a side arm 46 with valve means 48 of known type at a proximal end of the side arm 46, and with the inflation lumen 34 extending through the side arm 46 and communicating with the valve means 48. During use, the valve means 48 actuates by contact with the tip of a syringe (not shown) in order to permit passage of fluid through the valve means 48. The catheter 30 also has an annular sleeve 50 having opposed ends 52 and 54. The catheter 30 may be constructed from any suitable elastic material, such as silicone rubber.

As shown, the distal end portion 42 of the catheter 30 has en elongated annular groove 56 with a length approximately equal to the length of the sleeve 50, such that the groove 56 receives the sleeve 50 with the outer surface of the sleeve 50 being generally flush with adjacent portions of the catheter 30. The catheter 30 has an inflation opening 58 beneath the sleeve 50 and communicating with the inflation lumen 34. As shown, the catheter 30 has spaced proximal and distal circumferential bonding zones 60 and 62 located adjacent the opposed ends 52 and 54 of the sleeve 50 in order to secure the ends 52 and 54 of the sleeve 50 to the distal end portion 42 of the catheter 30. The catheter 30 also has longitudinal bonding lines 64 and 66 on opposed sides of the catheter 30 extending a substantial distance between the zones 60 and 62 in order to secure the sleeve 50 to the distal end portion 42 of the catheter 30 along the lines 64 and 66. In the present form, the lines 64 and 66 are interrupted in central regions 68 and 70, respectively, to permit passage of inflation fluid from the opening 58 to opposed sides of the catheter 30 beneath the sleeve 50. As shown, the inflation opening 58 is located intermediate the opposed lines 64 and 66. The bonding zones 60 and 62 and bonding lines 64 and 66 may be formed by a suitable adhesive intermediate the sleeve 50 and the distal end portion 42 of the catheter 30.

The catheter 30 has a pair of drainage eyes 72 and 74 communicating with the drainage lumen 36 on opposed sides of the catheter 30 at a location proximal the sleeve 50. As shown, the drainage eyes 72 and 74 are generally aligned with the bonding lines 64 and 66. In the present form, the drainage lumen 36 may terminate at a location proximal the sleeve 50.

In use, the catheter 30 is passed through the urethra of a patient until the sleeve 50 is located in the patient's bladder. Next, the tip of a syringe is contacted against the valve means 48 in order to actuate the valve means, and fluid is pumped from the syringe through the valve means 48, the inflation lumen 34, and the inflation opening 58 into the lower described portion of the sleeve 50, after which the fluid passes through the interrupted regions 68 and 70 to the upper portion of the sleeve 50 in order to inflate both halves of the sleeve 50. The inflated configuration of the sleeve 50 is illustrated in FIG. 6-8, in which the bonding lines 64 and 66 retain the sleeve 50 against the distal end portion 42 of the catheter 30, with the inflated sleeve forming a pair of opposed lobes 76 and 78 with drainage channels 80 and 82 being formed intermediate the lobes 76 and 78 on opposed sides of the catheter. After inflation of the sleeve 50 in the bladder, urine drains through the channels 80 and 82 to the drainage eyes 72 and 74 which are positioned by the inflated sleeve 50 adjacent the bladder neck. Thus, the particular sleeve 50 of the present invention permits drainage of urine to the drainage eyes 72 and 74 even though the drainage eyes 72 and 74 are located proximal the sleeve 50. From the drainage eyes 72 and 74, the urine drains through the drainage lumen 36 to a drainage tube (not shown) attached to the connector 44 of the catheter 30, and from the drainage tube to a drainage bag (not shown) for collection therein.

Thus, in accordance with the present invention, the drainage eyes 72 and 74 of the placed catheter are located adjacent the bladder neck in order to permit more complete drainage of the bladder during catheterization. Also, the placed catheter protrudes a shorter distance into the patient's bladder during catheterization, thus reducing the chance of irritation from the distal end of the catheter to the opposite bladder wall.

Another embodiment of the present invention is illustrated in FIG. 9, in which like reference numerals designate like parts. In this embodiment, the drainage lumen 36 extends to the distal end 40 of the catheter. The catheter 30 has a drainage eye 84 at the distal end 40 of the catheter 30, with the drainage eye 84 communicating with the drainage lumen 36 in addition to the drainage eyes proximal the sleeve 50 in order to permit more rapid drainage of urine from the bladder into the catheter 30.

Another embodiment of the present invention is illustrated in FIG. 10, in which like reference numerals designate like parts. In this embodiment, the bonding line 64' is uninterrupted longitudinally between the circumferential bonding zones 60 and 62. During inflation of the sleeve 50, fluid passes from the inflation opening 58 through the interrupted region 70 on the opposed side of the catheter 30 to inflate both halves of the sleeve 50.

Figure 12:
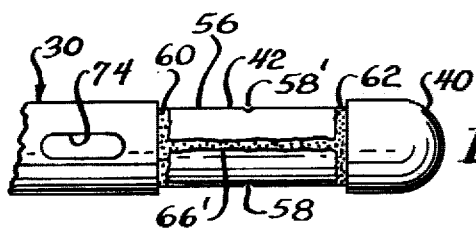
Figure 13:
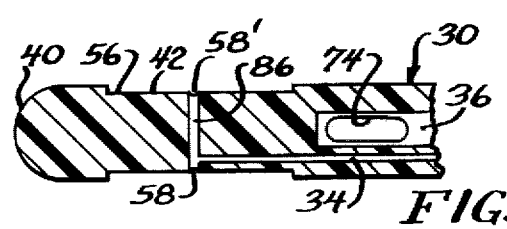
FIG. 13 is a fragmentary sectional view of the catheter of FIGS. 11 and 12.
Figure 18:
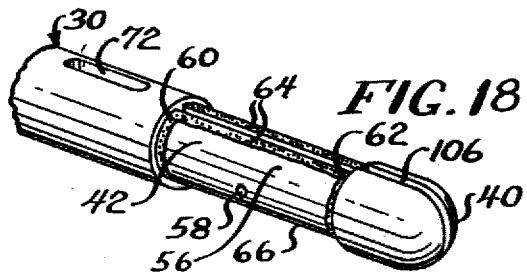
FIGS. 18 and 19 are fragmentary perspective views taken from opposed sides of the catheter of another embodiment of the catheter of the present invention.

Another embodiment of the present invention is illustrated in FIGS. 11-13, in which like reference numerals designate like parts. In this embodiment, the catheter 30 has an uninterrupted bonding line 64' on one side of the catheter extending between the circumferential bonding zones 60 and 62. On the other side of the catheter, the catheter 30 has an uninterrupted bonding line 66' extending between the circumferential bonding zones 60 and 62. The catheter 30 has an inflation opening 58 located beneath the lower portion of the sleeve and the inflation lumen 34 has a passageway 86 extending across the catheter to an inflation opening 58' located beneath an upper portion of the sleeve. Thus, the inflation lumen 34 communicates with both inflation openings 58 and 58' to simultaneously inflate the lower and upper portions of the sleeve on opposed sides of the bonding lines 64' and 66'.

Figure 14:
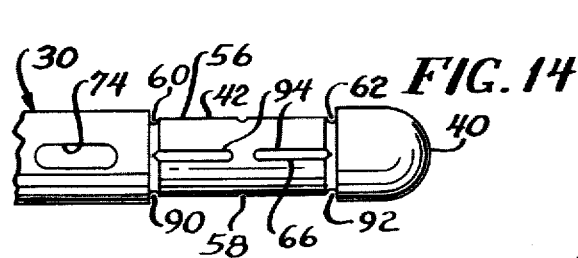
FIG. 14 is a fragmentary elevational view of another embodiment of the catheter of the present invention.
Figure 19:
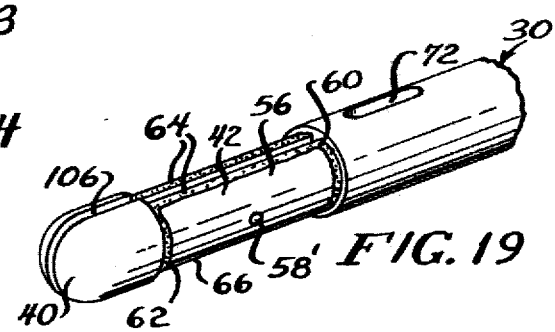
Figure 15:
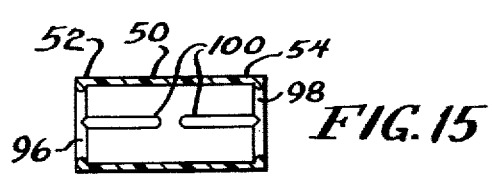
FIG. 15 is a sectional view of a sleeve for the catheter of FIG. 14.
Figure 20:
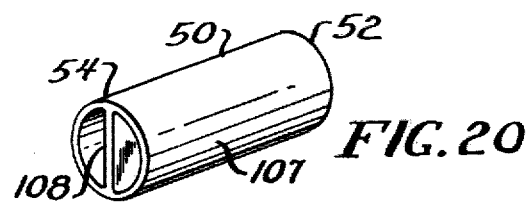
FIG. 20 is a perspective view of a sleeve for the catheter of FIGS. 18 and 19.

Another embodiment of the present invention is illustrated in FIGS. 14 and 15, in which like reference numerals designate like parts. In this embodiment, the catheter 30 has circumferential grooves 90 and 92 in the region of the circumferential bonding zones 60 and 62, respectively. The catheter 30 also has longitudinal grooves 94 on opposed sides of the catheter 30 extending between the grooves 90 and 92 in the region of the bonding lines 64 and 66. The sleeve 50 has inwardly directed circumferential ribs 96 and 98 at the opposed ends 52 and 54, respectively, of the sleeve 50, such that the ribs 96 and 98 are received in the grooves 90 and 92, respectively, when the sleeve 50 is placed in the annular groove 56. Also, the sleeve 50 has longitudinal ribs 100 on opposed sides of the sleeve 50 to be received in the grooves 94 of the catheter when the sleeve 50 is placed in the annular groove 56. During construction of the catheter, adhesive is placed in the grooves 90, 92, and 94, such that the ribs 96, 98, and 100 are bonded to the grooves 90, 92, and 94, respectively, in order to obtain an improved bond of the sleeve 50 to the distal end portion 42 of the catheter 30.

Figure 16:
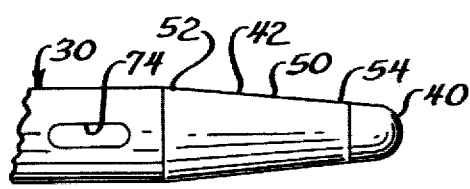
FIG. 16 is a fragmentary elevational view of another embodiment of the catheter of the present invention.
Figure 21:
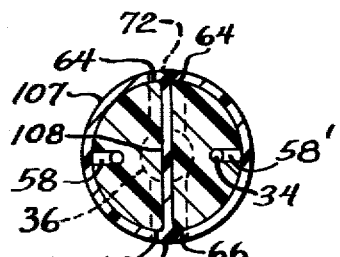
FIG. 21 is a sectional view of the catheter of FIGS. 18-20.

Another embodiment of the present invention is illustrated in FIG. 16, in which like reference numerals designate like parts. In this embodiment, the distal end portion 42 of the catheter 30 may be tapered toward the distal end 40, since the distal end portion 42 adjacent the distal end 40 in this embodiment does not contain a portion of the drainage lumen. The tapered distal end portion 42 of the catheter 30 facilitates insertion of the catheter through the patient's urethra during placement of the catheter.

Figure 17:
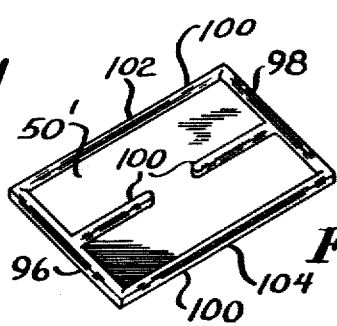
FIG. 17 is a perspective view of another embodiment of a sleeve for the catheter of the present invention.

Another embodiment of the present invention is illustrated in FIG. 17, in which like reference numerals designate like parts. In this embodiment, the sleeve 50' is formed in a flat configuration with opposed longitudinal edges 102 and 104. The sleeve 50' has opposed inwardly directed ribs 96 and 98, and a central longitudinal rib 100 extending between the ribs 96 and 98, and opposed longitudinal ribs 100 extending between the ribs 96 and 98 at the longitudinal edges 102 and 104 of the sleeve 50'. During construction, the sleeve 50' is wrapped about the catheter until the edges 102 and 104 abut each other with the sleeve 50' extending circumferentially around the catheter, and the ribs of the sleeve 50' are adhered into corresponding grooves of the catheter.

Another embodiment of the present invention is illustrated in FIGS. 18–21, in which like reference numerals designate like parts. In this embodiment, the catheter 30 has an elongated slit 106 in the distal end portion 42 of the catheter including the region of the elongated annular groove 56. The catheter 30 also has a pair of inflation openings 58 and 58' communicating with the inflation lumen and with the groove 56 on opposed sides of the slit 106. The catheter 30 has proximal and distal circumferential bonding zones 60 and 62 at opposed ends of the annular groove 56. The catheter 30 also has bonding lines 64 and 66 on both sides of the slit 106 at opposite ends of the slit 106. The sleeve 50 has an annular portion 107, and a central web 108 extending across the sleeve 50. During construction of the catheter 30, the web 108 is received in the slit 106, and the annular portion 107 of the sleeve 50 is received in the annular groove 56. The circumferential bonding zones 60 and 62 bond the opposed ends 52 and 54 of the sleeve 50 to the catheter 30, while the bonding lines 64 and 66 bond the annular portion 107 of the sleeve 50 to the catheter 30 adjacent opposed ends of the web 108. During use, the two halves of the sleeve 50 are inflated through the opposed inflation openings 58 and 58' communicating with the inflation lumen 34.

The foregoing detailed description is given for clearness of understanding only, and no unnecessary limitations should be understood therefrom, as modifications will be obvious to those skilled in the art.

I claim:

1. A catheter, comprising:
   an elongated shaft having an inflation lumen extending along the shaft, and a drainage lumen extending through the shaft, said catheter having a proximal end, a distal end, and a distal end portion;
   an elastic sleeve on the distal end portion of the catheter and having opposed ends; and
   means bonding the sleeve to said distal end portion in spaced circumferential zones adjacent the opposed ends of the sleeve and along longitudinal lines at least a substantial distance between said zones on opposed sides of said distal end portion, said catheter having an inflation opening beneath the sleeve communicating with the inflation lumen, and at least one drainage eye proximal the sleeve and communicating with the drainage lumen.

2. The catheter of claim 1 wherein said inflation opening is located intermediate said lines.

3. The catheter of claim 1 wherein said catheter has only one inflation opening.

4. The catheter of claim 1 wherein both of said lines are interrupted adjacent a central portion intermediate said zones.

5. The catheter of claim 1 wherein one of said lines is uninterrupted intermediate said zones, and the other of said lines is interrupted adjacent a central portion intermediate said zones.

6. The catheter of claim 1 wherein both of said lines are uninterrupted intermediate said zones, and in which the catheter has a pair of inflation openings communicating with the inflation lumen, said openings being located intermediate said lines on opposed sides of the catheter.

7. The catheter of claim 1 wherein said catheter has a pair of drainage eyes communicating with the drainage lumen on opposed sides of the catheter, said eyes being located proximal the sleeve and being generally aligned with said lines.

8. The catheter of claim 1 wherein the distal end portion is tapered toward the distal end of the catheter.

9. The catheter of claim 1 wherein the drainage lumen extends to the distal end of the catheter, and including a drainage eye at the distal end of the catheter communicating with the drainage lumen.

10. The catheter of claim 1 wherein the bonding means comprises adhesive.

11. The catheter of claim 1 wherein the bonding means comprises grooves in said zones and along said lines in said distal end portion, inner ribs on the sleeve along said zones and lines received in said grooves, and adhesive intermediate said grooves and ribs.

12. The catheter of claim 1 including an elongated annular groove in the distal end portion to receive said sleeve.

13. The catheter of claim 1 wherein the sleeve has opposed longitudinal edges abutting each other when the sleeve is wrapped about and secured to said distal end portion.

14. A catheter, comprising:
   an elongated shaft having an inflation lumen extending along the shaft, and a drainage lumen extending through the shaft, said catheter having a proximal end, a distal end, a distal end portion, an elongated slit extending through the catheter in said distal end portion, a pair of inflation openings in distal end portion on opposed sides of said slit and communicating with the inflation lumen;
   an elastic sleeve having opposed ends, an annular portion and a central web received in said slit on said distal end portion; and
   means bonding the sleeve to said distal end portion in spaced circumferential zones adjacent the opposed ends of the sleeve and along longitudinal lines extending between the zones on opposed sides of each end of the slit, said catheter having at least one drainage eye proximal said slit and communicating with the drainage lumen.

* * * * *